United States Patent [19]

Joerg et al.

[11] Patent Number: 5,142,087
[45] Date of Patent: Aug. 25, 1992

[54] PROCESS FOR THE PREPARATION OF DIALKYL CARBONATES

[75] Inventors: Klaus Joerg, Limburgerhof; Franz-Josef Mueller, Wachenheim; Wolfgang Harder, Weinheim; Rudolf Kummer, Frankenthal, all of Fed. Rep. of Germany

[73] Assignee: BASF Aktiengesellschaft, Ludwigshafen, Fed. Rep. of Germany

[21] Appl. No.: 564,324

[22] Filed: Aug. 8, 1990

[30] Foreign Application Priority Data

Aug. 12, 1989 [DE] Fed. Rep. of Germany ....... 3926709

[51] Int. Cl.$^5$ .............................................. C07C 69/96
[52] U.S. Cl. .................................................... 558/277
[58] Field of Search ................................ 558/260, 277

[56] References Cited

U.S. PATENT DOCUMENTS

| | | | |
|---|---|---|---|
| Re. 29,338 | 8/1977 | Perotti et al. | 558/260 |
| 3,846,468 | 11/1974 | Perotti et al. | 558/260 |
| 3,952,045 | 4/1976 | Gaenzler et al. | 558/260 |
| 4,218,391 | 8/1980 | Romano et al. | 558/260 |
| 4,318,862 | 3/1982 | Romano et al. | 558/260 |
| 4,370,275 | 1/1983 | Stammann et al. | 558/260 |
| 4,604,242 | 8/1986 | Harley et al. | 558/260 |
| 4,636,576 | 1/1987 | Bhattacharya et al. | 558/260 |
| 4,638,076 | 1/1987 | Bhattacharya | 558/260 |
| 4,761,467 | 8/1988 | Bhattacharya | 558/260 |

FOREIGN PATENT DOCUMENTS

| | | | |
|---|---|---|---|
| 0134668 | 10/1985 | European Pat. Off. | 558/260 |
| 0217651 | 10/1987 | European Pat. Off. | 558/260 |
| 2110194 | 3/1971 | Fed. Rep. of Germany | 558/260 |
| 2334736 | 8/1975 | Fed. Rep. of Germany | 558/260 |
| 2743690 | 9/1978 | Fed. Rep. of Germany | 558/260 |
| 3045767 | 7/1981 | Fed. Rep. of Germany | 558/260 |
| 45-11129 | 11/1970 | Japan | 558/260 |

OTHER PUBLICATIONS

Chem. Abstr. vol. 73 (1970) 14236a.

J. Org. Chem., vol. 35, No. 9 (1970) 2976-2978.

Primary Examiner—Mary C. Lee
Assistant Examiner—Robert C. Whittenbaugh
Attorney, Agent, or Firm—John H. Shurtleff

[57] ABSTRACT

A process for the continuous synthesis of dialkyl carbonates of the general formula I $$R-O-\underset{\underset{O}{\|}}{C}-OR \qquad (I)$$

in which R denotes $C_1$-$C_4$-alkyl, by reaction of $C_1$-$C_4$-alkanols with carbon monoxide and oxygen at elevated temperature and pressure and in the presence of a copper-containing catalyst dissolved or suspended in the reaction medium, wherein a) a gas stream containing carbon monoxide and oxygen is bubbled through the alkanol/catalyst mixture present in the reactor at a rate of from 1 to 100 liters per hours per gram of copper present in the reactor, part of which gas stream reacts with the alkanol to form dialkyl carbonate and water, which components are continuously entrained, together with alkanol, as a gaseous mixture, from the reaction mixture by means of the remaining, unreacted portion of the carbon monoxide/oxygen gas stream, whereupon b) the resulting gaseous mixture is separated, in a separator, into gaseous and liquid phases, the gaseous phase being recycled to the reactor if desired, and c) the liquid phase, which essentially consists of dialkyl carbonate, water and alkanol, is separated into its components, the dialkyl carbonate being isolated and the alkanol, if desired, recycled to the reactor, and d) the liquid in the reactor is replenished by adding fresh or recycled alkanol at the rate at which the alkanol is consumed and discharged.

16 Claims, No Drawings

PROCESS FOR THE PREPARATION OF DIALKYL CARBONATES

The present invention relates to a process for the continuous synthesis of dialkyl carbonates of the general formula I

in which R is $C_1$-$C_4$-alkyl, by reaction of $C_1$-$C_4$-alkanols with carbon monoxide and oxygen at elevated temperature and pressure and in the presence of a copper-containing catalyst dissolved or suspended in the reaction medium.

Dialkyl carbonates are used, inter alia, for the preparation of special monomers and for carbonylation and alkylation of high-grade organic intermediates. For example, dimethyl carbonate serves as a starting material for polycarbonates, as an intermediate for active substances and as a solvent for cellulose derivatives.

In recent years, a number of processes has been developed for the preparation of dialkyl carbonates by catalytic conversion of an alkanol with carbon monoxide and oxygen.

JP-45/11,129 (1970) makes use of divalent copper salts, in particular copper(II) chloride, as catalyst. The yield obtained with this process is very low, and in the highly acidic reaction solution, in which the copper salt forms strongly acidic cation acids with water, a major portion of the methanol is converted to undesirable by-products such as methyl chloride and dimethyl ether. For this reason, no use is made of this process industrially.

In DE-A 2,110,194, use is made of copper catalysts in which the copper has been complexed by means of organic complexing agents. Due to the redox reaction which occurs as conversion proceeds, the copper ions may be present as a mixture of monovalent and divalent copper. This process produces good yields under laboratory conditions but suffers from the disadvantage that the said complex catalysts are very expensive and are sensitive to the action of water and carbon dioxide, which causes decomposition thereof and leads to precipitation of copper carbonate. Furthermore, isolation and purification of the end products is particularly problematic. Consequently, this process is also unsuitable for production on an industrial scale.

For this reason, DE-A 2,743,690 uses simple salts of monovalent copper as catalyst instead of complex copper compounds. This process also provides good yields of dialkyl carbonates, but considerable problems arise when working up the end products on an industrial scale.

According to the teaching of the above patent, the catalyst is removed from the reaction product by filtration or centrifugation in the case of a suspended catalyst, or by rectification and crystallization in the case of a dissolved catalyst. Due to the fact that the catalyst-containing reaction solutions are highly corrosive, the isolation of the end product and the catalyst necessitates the use of high-grade apparatus. For example, all parts of the plant which come into contact with the catalyst-containing solutions, such as tanks, pipe-lines and equipment used for distillation, crystallization or filtration, must be lined with non-corrodible materials such as industrial ceramics, enamel, Teflon or tantalum, and even so there are still corrosion problems at the pumps and valves to be solved. This process is, therefore, uneconomical.

The process proposed in DE-A 3,045,767, which differs from the patent just cited only in the use of synthesis gas, presents the same working-up problems, which make the process unattractive economically. Similarly, the corrosion problems caused by the copper catalysts used in the following processes make said processes economically unattractive for use on an industrial scale: EP-A 271,651 [copper(methoxy) chloride catalyst together with nitrogenous co-solvents], U.S. Pat. No. 4,638,076 (phosphorus amides used as co-solvents for the copper catalyst), U.S. Pat. No. 4,636,576 (cyclic amides used as co-solvents), U.S. Pat. No. 4,604,242 (copper pentane/dionate complexes used as catalysts), U.S. Pat. No. 4,370,275 (copper complexes with nitrogen bases) and DE-A 2,334,736 (copper complexes with organic phosphorus compounds).

As an alternative to the removal of the catalyst via a catalyst circuit, EP-A 134,668 teaches a different technique in which the target dialkyl carbonate is placed in the reactor together with the catalyst to form a suspension into which a gas stream consisting of carbon monoxide, oxygen and inert gas is continuously passed together with the alkanol to be converted. The water of reaction is continuously distilled off as an azeotrope with the dialkyl carbonate, from which the water is then removed. Since more dialkyl carbonate is required to form the said azeotrope than is produced by the reaction, a portion of the dialkyl carbonate which has been distilled off azeotropically must be recycled to the reactor. To ensure that the removal of water is executed as effectively as possible, i.e. to avoid energy-consuming recycling of large amounts of dialkyl carbonate, it is necessary for the alkanol concentration in the reaction mixture to be as low as possible, preferably below 5% w/w. The consequence of this low concentration of the alkanol reactant in the reaction medium is a big drop in space-time yield. Thus only a modest space-time yield of 15 g/l. h is achieved. Since U.S. Pat. No. 4,360,477 involves virtually the same working-up technique, the above statements concerning process economy equally apply to this process.

Thus it is an object of the present invention to provide a process for the preparation of a dialkyl carbonate from an alkanol and carbon monoxide and oxygen which makes it possible to manufacture dialkyl carbonate on an industrial scale continuously and economically and, in particular, in high space-time yields, without it being necessary to recycle the corrosive catalyst.

Accordingly, we have found a process for the continuous synthesis of dialkyl carbonates of the general formula I

in which R denotes $C_1$-$C_4$-alkyl, by reaction of $C_1$-$C_4$-alkanols with carbon monoxide and oxygen at elevated temperature and pressure and in the presence of a copper-containing catalyst dissolved or suspended in the reaction medium, wherein a) a gas stream containing carbon monoxide and oxygen is bubbled through the alkanol/catalyst mixture present in the reactor at a rate of from 1 to 100 liters (STP) per hour per gram of copper present in the reactor, part of which gas stream reacts with the alkanol to form dialkyl carbonate and water, which components are continuously entrained, together with alkanol, as a gaseous mixture, from the reaction mixture by means of the remaining, unreacted portion of the carbon monoxide/oxygen gas stream, whereupon b) the resulting gaseous mixture is separated, in a separator, into gaseous and liquid phases, the gaseous phase being recycled to the reactor if desired, and c) the liquid phase, which essentially consists of dialkyl carbonate, water and alkanol, is separated into its components, the dialkyl carbonate being isolated and the alkanol, if desired, recycled to the reactor, and d) the liquid in the reactor is replenished by adding fresh or recycled alkanol at the rate at which the alkanol is consumed and discharged.

The dialkyl carbonates (I) are formed by the reaction of an alkanol ROH with carbon monoxide and oxygen, preferably in the presence of a copper catalyst, as formally represented by the following equation (1) [cf. Saegusa et al. In J. Org. Chem., 35, 2976 (1970)]:

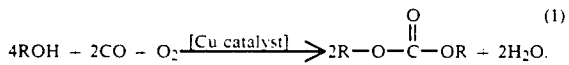

In the process of the invention, the alkanol to be converted is placed in the reactor together with the catalyst, and the reaction gases carbon monoxide and oxygen, diluted, if desired, with inert gas, are bubbled through the said reaction mixture. The dialkyl carbonate and water formed during the reaction are entrained by the stream of gas comprising unreacted carbon monoxide and oxygen and are thus removed from the reaction mixture. The liquid reaction medium essentially comprises the alkanol to be converted. The molar ratio of alkanol to dialkyl carbonate to catalyst (standardized to 1 mole of alkanol) in the reaction medium is, in general, 1:(0.03–1):(0.01–0.33), advantageously 1:(0.05–0.5):(0.01–0.1) and preferably 1:(0.1–0.2):(0.01–0.05), the catalyst being calculated as the amount of Cu present in the reaction medium.

The reaction can be carried out at even lower catalyst contents in the reaction mixture, but this leads to lower space-time yields. Higher catalyst concentrations, on the other hand, produce no further economical improvement despite the use of larger amounts of catalyst.

As regards the content of dialkyl carbonate in the reaction mixture, it is desirable to aim at the removal of the dialkyl carbonate and water of reaction from the reaction mixture as soon as these are formed, i.e. the general aim is to maintain a low steady-state concentration of dialkyl carbonate in the reactor. The reaction may, if desired, be carried out at higher steady-state concentrations of dialkyl carbonate, but this complicates the measures necessary to isolate the product and involves a reduction in space-time yield.

Such low steady-state concentrations of dialkyl carbonate in the reaction mixture, coupled with high space-time yields, are achieved, according to the invention, by passing the reaction gases comprising carbon monoxide and oxygen through the reaction mixture at a rate of, advantageously, from 1 to 100, preferably from 10 to 50 and more preferably from 20 to 30, liters (STP) per hour per gram of copper present in the reaction mixture in the form of copper catalyst. Under the conditions of the reaction, dialkyl carbonate and water are formed almost exclusively from a portion of the reaction gases, whilst the remaining portion thereof serves to entrain from the reaction mixture the thus formed dialkyl carbonate and the water of reaction and sufficient alkanol to form the required azeotrope. This is made possible by controlling the rate of the $CO/O_2$ gas mixture such that the dialkyl carbonate and water are formed at a rate which enables a low-boiling ternary azeotrope of dialkyl carbonate, water and alkanol to be formed.

This procedure, besides simplifying the isolation of the end product (dialkyl carbonate), has a favorable influence on the productivity of the reaction due to an advantageous shift of reaction equilibrium and also results in a low steady-state concentration of the water of reaction in the reaction mixture. The latter is generally less than 5% and is advantageously less than 1%, by weight of the reaction mixture. This suppresses side reactions such as the formation of carbon dioxide and successive deactivation of the catalyst with the formation of copper carbonates.

It is, of course, possible to control the rate of flow of the reaction gases, which may contain inert gas if desired, such that more alkanol is entrained from the reaction mixture than is necessary to form the said ternary azeotrope. However, this procedure can effect an increase in energy costs.

The reaction of the gaseous reactants with the alkanol may be carried out under atmospheric or elevated pressure. In general, pressures of from 1 to 50 bar and preferably from 15 to 30 bar are used, the temperature being from 80° to 200° C., preferably from 90° to 130° C. The pressure is advantageously achieved by compression of the reaction gases.

The molar ratio of carbon monoxide to oxygen in the reaction gas can be varied within wide limits, but it is advantageous to set it at from 1:0.01 to 1:0.5. Within this range, the oxygen partial pressure is sufficiently high to provide economical space-time yields, whilst on the other hand the oxygen content is sufficiently low to avoid the risk of the formation of explosive carbon monoxide/oxygen gas mixtures.

The reaction gas comprising carbon monoxide and oxygen may, if necessary, contain added inert gas. This is particularly advantageous in cases in which the carbon monoxide/oxygen gas mixture used would otherwise be explosive. The addition of suitable amounts of inert gas protects such mixtures from explosion.

The catalysts used in the process of the invention are copper catalysts based on copper (I) and/or copper (II) salts. Since the reaction represented by equation (1) is a redox reaction, both types of copper ion will be present in the reaction mixture at the same time. The copper salt catalysts used are preferably individual or mixed copper salts such as copper (I) and/or copper (II) halides, copper (I) or copper (II) sulfate, copper (II) ($C_1$–$C_4$-alkoxy) halides such as copper (methoxy) chloride, copper (ethoxy) chloride, copper(butoxy) chloride and copper (mthoxy) bromide. When a copper (alkoxy) halide is used, it is advantageous to select one in which the alkoxy moiety corresponds to the alkanol to be converted, as otherwise mixed dialkyl carbonates will be formed, which is not generally desirable. We particularly prefer to run the process of the invention with a copper (I) halide, especially copper (I) chloride, and/or a copper (alkoxy) halide corresponding to the alkanol to be converted. The copper catalyst is generally used in a concentration of from 0.1 to 10, preferably from 0.3 to 3 and more preferably from 0.3 to 1.5, moles per liter of alkanol. Since the catalytically active copper salts are only moderately soluble in the alkanols, these catalyst concentrations frequently lead to the formation of catalyst suspensions.

Under the reaction conditions stated above and at a feed rate of 50 l of $CO/O_2$ gas mixture (STP) per hour, for example, the space-time yields obtained in the synthesis of, say, dimethyl carbonate may be from 20 to 75 and advantageously from 40 to 60 g of product isolated and discharged from the reaction mixture per hour per liter of reaction mixture.

The process of the invention is suitable for the preparation of $C_1$-$C_4$-dialkyl carbonates such as dimethyl carbonate, diethyl carbonate, di-n-propyl carbonate, di-isopropyl carbonate and dibutyl carbonates. It is particularly useful for the synthesis of diethyl carbonate and, especially, dimethyl carbonate.

Apart from providing improved space-time yields, as mentioned above, the process of the invention has the very special advantage that the highly corrosive catalyst, which is only partially dissolved in the alkanol, is kept in the reactor throughout the continuous reaction. This dispenses with all problems incurred in operations involving the use of a special catalyst circuit, such as corrosion of the separating means, difficulty of obtaining perfect seals when using special materials, erosion, choking, etc.. When operating by the method of the invention, only the reactor needs to be made of, or lined with, special material such as industrial ceramics, enamel, Teflon or glass. Thus the costs involved by our method are significantly lower than is the case with prior art methods.

EXAMPLE 1

Preparation of dimethyl carbonate

In a plant such as is illustrated diagramatically in the accompanying drawing, methanol was reacted with oxygen under a pressure of 25 bar and at a temperature of 120° C. The catalyst was copper(methoxy) chloride, used in an amount of 0.7 mole/l of methanol. The reactor was a bubbler reactor of pressure-resistant glass (volume 0.13 liter) provided with a stirrer. The reaction gases were bubbled through the column from the bottom, and the reaction medium was agitated by the movement of the stirrer and of the said gases.

At a throughput rate of 60 liters of CO and 3 liters of $O_2$ per hour per liter of reaction mixture, the space-time yield was 25-32 g of dimethyl carbonate per hour per liter. The catalyst showed no loss of activity after an on-stream period of 100 hours.

The dimethyl carbonate formed was removed from the reaction mixture in gaseous form together with the water of reaction and sufficient methanol to form the ternary azeotrope. This gas stream was separated into its liquid and gaseous components in a separator at 5° C. The liquid effluent comprised dimethyl carbonate (17% w/w), water (3-5% w/w) and methanol (78-80% w/w) plus traces of formaldehyde dimethylacetal (<0.2% w/w). The methanol was converted to dimethyl carbonate at a conversion rate of 13%, the selectivity being 98-100%. The $CO/O_2$ mixture withdrawn at the top separator (60-65 l/h) contained from 0.4 to 3% of $O_2$ and less than 0.05% of $CO_2$, the remainder being CO.

EXAMPLE 2

Example 1 was repeated except that the throughput of $CO/O_2$ was adjusted to 110 liters of CO and 2.6 liters of $O_2$ per hour per liter of reaction mixture. Under these conditions, the space-time yield was 54 g of dimethyl carbonate per liter per hour. At a methanol conversion rate of 16-17%, its selectivity for dimethyl carbonate was virtually quantitative. The off-gas from the condensation contained only CO (97.6-99.6% v/v) and $O_2$ (0.4-2.4% v/v) and could be recycled. No formation of by-products such as carbon dioxide, methyl chloride or dimethyl ether was found to have taken place.

We claim:

1. In a process for the continuous synthesis of a dialkyl carbonate of the formula

in which R is $C_1$-$C_4$-alkyl, by reaction of a $C_1$-$C_4$-alkanol with carbon monoxide and oxygen at elevated temperature and pressure and in the presence of a copper-containing catalyst dissolved or suspended in the reaction medium, the improvement which comprises:
 (a) continuously bubbling a gas stream containing carbon monoxide and oxygen through a reactor, in which the alkanol/catalyst mixture is maintained as a liquid reaction medium, at a rate of 1 to 100 liters (STP) per hour per gram of copper present in the reactor, reacting part of said gas stream with the alkanol to form dialkyl carbonate and water as reaction products which are continuously entrained and discharged together with alkanol, as a gaseous mixture, from the reactor by means of the remaining, unreacted portion of the carbon monoxide/oxygen gas stream such that the dialkyl carbonate and water of reaction are removed from the reaction mixture as they are formed;
 (b) separating the resulting gaseous mixture, as discharged from the reactor, in a separator into gaseous and liquid phases;
 (c) separating the liquid phase, which consists essentially of dialkyl carbonate, water and alkanol, into its components to isolate the dialkyl carbonate; and
 (d) replenishing the liquid reaction mixture in the reactor by adding said alkanol at the rate at which it is consumed and discharged.

2. A process as claimed in claim 1, wherein the molar ratio of alkanol to copper-containing catalyst is from 3:1 to 330:1.

3. A process as claimed in claim 1, wherein the $CO/O_2$ mixture used contains CO and $O_2$ in a molar ratio of from 1:01 to 1:0.5.

4. A process as claimed in claim 1, wherein the catalyst used is copper (methoxy) chloride.

5. A process as claimed in claim 1, wherein the catalyst used is copper(I) chloride.

6. A process as claimed in claim 1, wherein the alkanol used is methanol.

7. A process as claimed in claim 1, wherein the dialkyl carbonate concentration produced in the reactor is maintained sufficiently low to form a low boiling ternary azeotrope with the water and the unreacted alkanol for entrainment and discharge with said unreacted portion of the carbon monoxide/oxygen gas stream.

8. A process as claimed in claim 7, wherein the gaseous phase and the alkanol of the liquid phase, as obtained from the separator and isolated as separate components, are recycled to the reactor.

9. A process as claimed in claim 7, wherein the concentration of the water of reaction produced in the reactor is maintained at a level of less than about 5% by weight of the reaction mixture.

10. A process as claimed in claim 9, wherein the concentration of the water of reaction produced in the reactor is maintained at a level of less than about 1% by weight of the reaction mixture.

11. A process as claimed in claim 1, wherein the gaseous phase from the separator is recycled to the reactor.

12. A process as claimed in claim 1, wherein the alkanol isolated from the liquid phase, as obtained from the separator, is recycled to the reactor.

13. A process as claimed in claim 1, wherein the reaction of said alkanol with the carbon monoxide and oxygen is carried out at a temperature of about 80° to 200° C. and under a pressure of about 1 to 50 bar.

14. A process as claimed in claim 1, wherein the reaction of said alkanol with the carbon monoxide and oxygen is carried out at a temperature of about 90° to 130° C. and under a pressure of about 15 to 30 bar.

15. A process as claimed in claim 1, wherein said gas stream containing carbon monoxide and oxygen is bubbled through the liquid reaction mixture in the reactor at a ratio of from 10 to 50 liters (STP) per hour per gram of copper present in the reactor.

16. A process as claimed in claim 1, wherein said gas stream containing carbon monoxide and oxygen is bubbled through the liquid reaction mixture in the reactor at a rate of from 20 to 30 liters (STP) per hour per gram of copper present in the reactor.

* * * * *